US00PP24611P3

(12) United States Plant Patent
Cain

(10) Patent No.: US PP24,611 P3
(45) Date of Patent: Jul. 8, 2014

(54) GRAPEVINE 'IFG FOURTEEN'

(50) Latin Name: *Vitis vinifera*
Varietal Denomination: IFG Fourteen

(71) Applicant: David Cain, Bakersfield, CA (US)

(72) Inventor: David Cain, Bakersfield, CA (US)

(73) Assignee: International Fruit Genetics, LLC, Bakersfield, CA (US)

( * ) Notice: Subject to any disclaimer, the term of this patent is extended or adjusted under 35 U.S.C. 154(b) by 103 days.

(21) Appl. No.: 13/573,778

(22) Filed: Oct. 5, 2012

(65) Prior Publication Data

US 2014/0101797 P1 Apr. 10, 2014

(51) Int. Cl.
*A01H 5/00* (2006.01)

(52) U.S. Cl.
USPC ..... Plt./205

(58) Field of Classification Search
USPC ..... Plt./205
See application file for complete search history.

*Primary Examiner* — Annette Para

(57) ABSTRACT

This invention is a new and distinct grapevine variety named 'IFG Fourteen' which is characterized by producing small round bright red berries having very crisp texture with a very strong muscat flavor and which ripens in midseason.

1 Drawing Sheet

Latin name of the genus and species claimed: *Vitis vinifera.* Variety denomination: 'IFG Fourteen'.

BACKGROUND OF THE INVENTION

The new and distinct grapevine described and claimed herein originated from a hand pollinated cross of the IFG 01077-096-221, an unnamed seedless selection from the IFG breeding program and the IFG 01054-082-202 another unnamed seedless selection from the IFG breeding program hybridized in May 2004. The abortive seed traces were subsequently embryo cultured and the resulting plant was planted in the field in April 2005. The present variety of grapevine was selected as a single plant in 2006 and was first asexually propagated by hardwood cuttings in December 2006 near Delano, Kern County, Calif. The resulting propagules were planted during April 2007 near Delano, Kern County, Calif. and were found to reproduce true-to-type through at least two generations of asexual reproduction using hardwood cuttings and grafting onto rootstocks.

BRIEF SUMMARY OF THE INVENTION

The new grapevine 'IFG Fourteen' is characterized by producing small round bright red berries having very crisp texture with a very strong muscat flavor and which ripens in midseason. Berries are borne on small to medium size clusters which are very compact and require gibberellin applications to thin clusters and size berries. Berries color extremely well and do not require chemical applications to achieve good color. 'IFG Fourteen' stores extremely well. Stems remain green and berries retain their crisp texture and strong muscat flavor for up to twelve weeks in cold storage. To the inventor's knowledge, the known variety to which the new grapevine variety is most similar is the Flame seedless variety (unpatented). 'IFG Fourteen' differs from the 'Flame Seedless' by ripening approximately three to four weeks later, having less waxy bloom and having a very strong flowery muscat flavor as opposed to the neutral flavor of 'Flame Seedless'.

'IFG Fourteen' differs from its maternal parent by producing brighter red, crisp berries that have a strong muscat flavor as opposed to the softer reddish black later ripening neutral flavored fruits of the IFG 01077-096-221. It differs from its pollen parent, by having later ripening, crisp red, muscat flavored berries as opposed to the early ripening black berries of the IFG 01054-082-202.

BRIEF DESCRIPTION OF THE FIGURE

The accompanying photographic illustration in FIG. 1 illustrates in full color 'IFG Fourteen'. The colors are as nearly true as is reasonably possible in a color representation of this type.

DETAILED BOTANICAL DESCRIPTION OF THE INVENTION

Throughout this specification, color names beginning with a small letter signify that the name of that color, as used in common speech, is aptly descriptive. Color names beginning with a capital letter designate values based upon R.H.S. Colour Chart, published by The Royal Horticultural Society, London, England.

Throughout this specification subjective description values conform to those set forth by the International Plant Genetic Resources Institute publication 'Descriptors for Grape' (*Vitis* spp.) (1983) which was developed in collaboration with the Office International de la Vigne et du Vin (OIV) and the International Union for the Protection of New Varieties of Plants (UPOV).

The descriptive matter which follows pertains to 'IFG Fourteen' plants grown in the vicinity of Delano, Kern County, Calif. during 2009, and 2010 and is believed to apply to plants of the variety grown under similar conditions of soil and climate elsewhere:

VINE

General:
- *Size*.—Medium.
- *Vigor*.—Medium to slightly weaker than average.
- *Density of foliage*.—Medium dense.
- *Productivity*.—Very productive.
- *Root stock*.—Own root.
- *Training method*.—Typically spur pruned leaving 2 bud spurs.

Trunk:
- *Trunk diameter of* 4-*year-old vines at* 30 *cm above the soil line*.—4.8 cm.
- *Shape*.—Medium stocky.
- *Straps*.—Short-Split.
- *Surface texture*.—Smooth.
- *Inner bark color*.—Can be any of the following colors; 165A, 164A, and 177C.

SHOOTS

Young shoot:
- *Form of tip*.—Wide open.
- *Distribution of anthocyanin coloration of tip*.—Absent.
- *Intensity of anthocyanin coloration of tip*.—Absent.
- *Density of prostrate hairs of tip*.—Medium.
- *Density of erect hairs of tip*.—Absent.
- *Color*.—Yellow-Green; can be any of the following colors; 153A and B, and N144A.

Woody shoots (mature canes):
- *Shape*.—Medium.
- *Internode length*.—Short to Medium; About 6.9 cm.
- *Width at node*.—About 1.3 cm.
- *Cross section*.—Elliptic.
- *Surface*.—Striate.
- *Main color*.—Yellowish-brown; can be any of the following colors; 166C and D, 164A and B, and 165B and C.
- *Density of erect hairs of nodes*.—None.
- *Density of erect hairs on internodes*.—None.
- *Growth of axillary shoots*.—Weak; Approximately 12.0 cm.

Flowering shoot:
- *Vigor during flowering*.—Medium.
- *Attitude during flowering on shoots not tied*.—Semi-erect-Horizontal.
- *Color*.—Dorsal side of internodes — Green.
- *Color*.—Ventral side of internodes — Green.
- *Color*.—Dorsal side of nodes — Green.
- *Color*.—Ventral side of nodes — Green.
- *Density of prostrate hairs of nodes*.—None-Very sparse.
- *Density of erect hairs of nodes*.—None.
- *Density of prostrate hairs on internode*.—Very sparse.
- *Density of erect hairs on internode*.—None.
- *Anthocyanin coloration of buds*.—Absent.

Tendrils:
- *Distribution on the shoot* (*at full flowering*).—Discontinuous.
- *Length of tendril*.—Medium; About 22.3 cm.
- *Thickness*.—Medium.
- *Color*.—Yellow-Green; can be any of the following colors; N144A, 144B, and 154A.
- *Form*.—mostly bifurcated, occasionally trifurcated or quadfurcated.
- *Number of consecutive tendrils*.—2.

LEAVES

Young leaves:
- *Color of upper surface of first four distal unfolded leaves*.—Green-Copper.
- *Average intensity of anthocyanin coloration of six distal leaves prior to flowering*.—Weak.
- *Density of prostrate hairs between veins* (*lower surface*) .—Sparse.
- *Density of prostrate hairs on veins* (*lower surface*).—Sparse.
- *Density of erect hairs between veins* (*lower surface*).—Sparse to Medium.
- *Density of erect hairs on veins* (*lower surface*).—Sparse.

Mature leaves:
- *Average length*.—About 14.2 cm.
- *Average width*.—About 18.3 cm.
- *Mature leaf size*.—Medium.
- *Shape of blade*.—Pentagonal.
- *Number of lobes*.—5.
- *Anthocyanin coloration of main veins on upper side of blade*.—Absent.
- *Mature leaf profile*.—Undulate.
- *Blistering surface of blade upper surface*.—Weak.
- *Leaf blade tip*.—Curved downwardly.
- *Undulation of margin*.—Pronounced.
- *Thickness*.—Medium.
- *Undulation of blade between main and lateral veins*.—Overall.
- *Shape of teeth*.—Mixture of both sides straight and both sides convex.
- *Length of teeth*.—Short.
- *Ratio length/width of teeth*.—Small.
- *Shape of upper lateral sinuses*.—Lobes strongly overlapping.
- *Depth of upper lateral sinuses*.—Medium.
- *General shape petiole sinus*.—Lobes half overlapping.
- *Shape of base of upper leaf sinuses*.—U-shaped.
- *Tooth at petiole sinus*.—Absent.
- *Density of prostrate hairs between veins on lower surface of blade*.—Sparse.
- *Density of erect hairs between veins on lower surface of blade*.—Medium.
- *Density of prostrate hairs on main veins on lower surface of blade*.—Sparse.
- *Density of erect hairs on main veins on lower surface of blade*.—Sparse-Medium.
- *Density of prostrate hairs on main veins on upper surface of blade*.—Sparse.
- *Density of erect hairs on main veins on upper surface of blade*.—None.
- *Autumn coloration of leaves, leaves can be a single color or combination of colors in a mottled pattern or on the edges of the leaves*.—Yellow-Green; 153A, Grey-Red; 178A and B, Grey-Purple; 183A and B, Grey-Orange; 163A and B.

Upper surface:
- *Color*.—Green; leaves can be any one of the following colors, depending on their location in the plant canopy; 146A and B, and 137B.
- *Anthocyanin coloration of main veins*.—Absent.
- *Surface appearance*.—Glossy to Semi-glossy.
- *Blistering surface of blade*.—Weak to Medium.

Lower surface:

*Color*.—Green: leaves can be any one of the following colors, depending on their location in the plant canopy; 146A and B.

*Anthocyanin coloration of main veins (lower surface)*.—Absent.

*Glossiness*.—Medium.

*Surface texture*.—Smooth.

*Surface appearance*.—Semi-glossy.

Petiole:

*Length*.—About 16.8 cm.

*Length of petiole compared to middle vein*.—Slightly longer.

*Density of prostrate hairs on petiole*.—Sparse.

*Density of erect hairs on petiole*.—None.

Buds:

*Bud fruitfulness*.—Basal: Mostly fruitful.

*Position of first fruitful shoot on previous season cane*.—$1^{st}$ to $2^{nd}$ node.

*Time of bud burst*.—Early; Feb. 18, 2010.

FLOWERS

General:

*Flower sex*.—Hermaphrodite.

*Length of first inflorescence*.—Medium; About 20.8 cm long by 8.2 cm wide.

*Position of first flowering and fruiting node*.—$2^{nd}$ to 3rd (current season growth).

*Number of inflorescence per flowering shoot*.—1.1 to 2.

*Time of bloom*.—Midseason as compared with similar varieties in the growing area of Delano, Calif.

*Date of full bloom*.—May 18, 2010.

FRUIT

General:

*Ripening period*.—Early; Approximately Aug. 9, 2010.

*Use*.—Fresh market.

*Keeping quality*.—Excellent, stores for up to 12 weeks.

*Resistance to*.—Insects: Average typical of Vitis vinifera species. Diseases: Average typical of *Vitis vinifera* species.

*Shipping quality*.—Excellent.

*Refractometer test*.—Solid-sugar: About 18.0 Brix.

*Brix/acid*.—About 31.0.

*Titratable acidity*.—About 0.58.

*Juice* $p^H$.—About 3.6.

Cluster:

*Mature cluster length (peduncle excluded)*.—About 19.9 cm.

*Mature cluster width*.—About 14.8 cm.

*Mature cluster weight*.—About 456 g.

*Bunch density*.—Medium.

*Number of berries*.—About 216.

*Form*.—Cylindrical-Conical.

Peduncle:

*Lignification of peduncle*.—Weak.

*Length of peduncle*.—Medium; Approximately 3.2 cm.

Berry:

*Uniformity of size*.—Uniform.

*Single berry weight*.—About 3.9 g natural to about 4.8 g when treated with gibberellic acid.

*Shape*.—Round.

*Seeds*.—Absent.

*Cross section*.—Circular.

*Berry dimensions*.—longitudinal axis: About 18.5 mm. Horizontal axis: About 17.7 mm.

*Berry firmness*.—very firm and crisp.

*Particular flavor*.—Muscat.

*Bloom (cuticular wax)*.—Weak.

*Berry separation from pedicel*.—Difficult.

*Skin color (without bloom)*.—Greyed-Purple; single berries can be a range of colors, depending on sun exposure and individual berry maturity; 59A, and 185A and B, and 187B and C.

Skin:

*Thickness*.—Medium.

*Texture*.—Medium.

*Reticulation*.—Absent.

*Tenacity*.—Tenacious to flesh.

What is claimed:

1. A new and distinct variety of grapevine as herein illustrated and described.

* * * * *

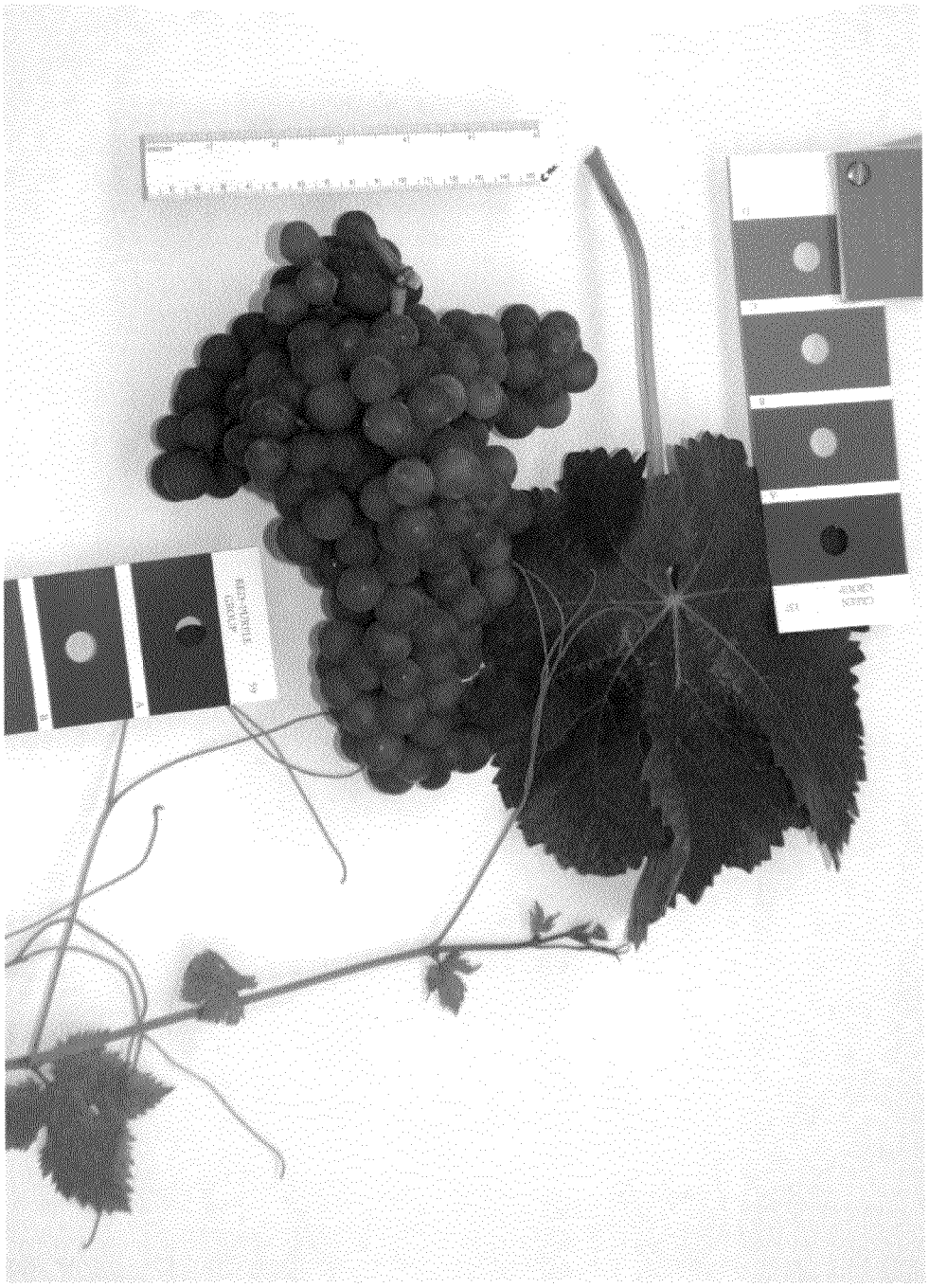
GREEN-WHITE
YELLOW
99
GREEN
GREY
159